(12) United States Patent
Hirata

(10) Patent No.: US 10,034,601 B2
(45) Date of Patent: Jul. 31, 2018

(54) HEAT RESISTANT SHEATH FOR ENDOSCOPE AND ENDOSCOPE SYSTEM PROVIDED WITH HEAT RESISTANT SHEATH FOR ENDOSCOPE

(71) Applicant: OLYMPUS CORPORATION, Tokyo (JP)

(72) Inventor: Yasuo Hirata, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 100 days.

(21) Appl. No.: 15/176,287

(22) Filed: Jun. 8, 2016

(65) Prior Publication Data

US 2016/0278623 A1    Sep. 29, 2016

Related U.S. Application Data

(63) Continuation of application No. PCT/JP2014/067729, filed on Jul. 3, 2014.

(30) Foreign Application Priority Data

Dec. 12, 2013  (JP) .................................. 2013-257314
May 20, 2014  (JP) .................................. 2014-104528

(51) Int. Cl.
*A61B 1/04* (2006.01)
*A61B 1/12* (2006.01)
(Continued)

(52) U.S. Cl.
CPC ................ *A61B 1/12* (2013.01); *A61B 1/005* (2013.01); *A61B 1/00135* (2013.01);
(Continued)

(58) Field of Classification Search
CPC . A61B 1/015; A61B 1/12; A61B 1/125–1/128
(Continued)

(56) References Cited

U.S. PATENT DOCUMENTS 5,339,800 A      8/1994  Wiita et al.
5,464,008 A  *  11/1995  Kim ................... A61B 1/00091
                                                         600/157
(Continued)

FOREIGN PATENT DOCUMENTS

JP      H04-258915 A    9/1992
JP      2008-073222 A   4/2008
(Continued)

OTHER PUBLICATIONS

International Search Report dated Oct. 7, 2014 issued in PCT/JP2014/067729.

*Primary Examiner* — Matthew J Kasztejna
(74) *Attorney, Agent, or Firm* — Scully, Scott, Murphy & Presser, P.C.

(57) ABSTRACT

A heat resistant sheath for endoscope includes a main body sheath into which an insertion portion of an endoscope apparatus is inserted, and into which a cooling fluid is supplied by a cooling device, a sheath distal end portion at which an endoscope distal end portion is arranged, and that is connected to a distal end of the main body sheath, an observation hole formed at a middle part of a circumferential side portion of the sheath distal end portion, and configured to expose an observation window of the endoscope distal end portion to allow observation of an object, and an exhaust hole formed in the circumferential side portion of the sheath distal end portion, on a distal end side with respect to the observation hole, and configured to discharge the cooling fluid in a direction different from an observation direction of the endoscope apparatus.

8 Claims, 17 Drawing Sheets

(51) Int. Cl.
　　　*G02B 23/24*　　(2006.01)
　　　*A61B 1/00*　　(2006.01)
　　　*A61B 1/005*　　(2006.01)
　　　*A61B 1/06*　　(2006.01)
　　　*A61B 1/07*　　(2006.01)
(52) U.S. Cl.
　　　CPC .............. *A61B 1/0661* (2013.01); *A61B 1/07* (2013.01); *A61B 1/125* (2013.01); *A61B 1/126* (2013.01); *A61B 1/127* (2013.01); *A61B 1/128* (2013.01); *G02B 23/24* (2013.01)
(58) Field of Classification Search
　　　USPC ................. 600/121–125, 155–158, 170–171
　　　See application file for complete search history.

(56) References Cited

U.S. PATENT DOCUMENTS

| 6,361,491 | B1 * | 3/2002 | Hasegawa | A61B 1/00096 |
| | | | | 348/45 |
| 7,121,098 | B2 * | 10/2006 | Hatcher | F23N 5/08 |
| | | | | 385/117 |
| 7,422,559 | B2 * | 9/2008 | Kehoskie | G02B 23/2492 |
| | | | | 348/82 |
| 8,001,984 | B2 * | 8/2011 | Sasaki | A61B 1/00091 |
| | | | | 134/102.1 |
| 9,046,694 | B2 * | 6/2015 | Hirata | G02B 23/2492 |
| 9,700,378 | B2 * | 7/2017 | Mowlai-Ashtiani | A61B 90/70 |
| 2008/0242927 | A1 * | 10/2008 | Hirata | G02B 23/2492 |
| | | | | 600/109 |
| 2009/0259103 | A1 | 10/2009 | Hirata | |
| 2013/0184531 | A1 * | 7/2013 | Kanzaki | A61B 1/00059 |
| | | | | 600/170 |

FOREIGN PATENT DOCUMENTS

| JP | 2008-281613 A | 11/2008 |
| JP | 2010-026391 A | 2/2010 |

* cited by examiner

__US 10,034,601 B2__

HEAT RESISTANT SHEATH FOR ENDOSCOPE AND ENDOSCOPE SYSTEM PROVIDED WITH HEAT RESISTANT SHEATH FOR ENDOSCOPE

CROSS REFERENCE TO RELATED APPLICATION

This application is a continuation application of PCT/JP2014/067729 filed on Jul. 3, 2014 and claims benefit of Japanese Applications No. 2013-257314 filed in Japan on Dec. 12, 2013, and No. 2014-104528 filed in Japan on May 20, 2014, the entire contents of which are incorporated herein by this reference.

BACKGROUND OF THE INVENTION

1. Field of the Invention

The present invention relates to a heat resistant sheath for endoscope, configured to guide an insertion portion of an endoscope apparatus, and an endoscope system provided with the heat resistant sheath for endoscope.

2. Description of the Related Art

Conventionally, endoscope apparatuses including an insertion portion which may be inserted into an object and which enables observation of the object that an observer cannot directly see by eye are being used. According to such an endoscope apparatus, at the time of insertion of the insertion portion into the object, an endoscope guide tube is sometimes externally attached to the insertion portion to guide the insertion portion.

With respect to such an endoscope guide tube, a technique is known, as disclosed in Japanese Patent Application Laid-Open Publication No 2010-26391, for example, according to which a heat resistant sheath into which an insertion portion is inserted to observe a high temperature environment is included, and cooling air is made to flow inside the heat resistant sheath so as to protect the insertion portion in the high temperature environment.

SUMMARY OF THE INVENTION

A heat resistant sheath for endoscope according to an aspect of the present invention includes a main body sheath having a substantially tubular shape into which at least a distal end side of an insertion portion of an endoscope apparatus is inserted, and into which a cooling fluid for cooling the insertion portion is supplied by a cooling device, a sheath distal end portion, having a bottomed cylindrical shape with a closed distal end, at which an endoscope distal end portion of the insertion portion inserted into the main body sheath is arranged, and that is connected to a distal end of the main body sheath, an observation hole formed at a middle part of a circumferential side portion of the sheath distal end portion, and configured to expose an observation window provided at a side portion of the endoscope distal end portion to allow observation of an object, and an exhaust hole formed in the circumferential side portion of the sheath distal end portion, on a distal end side with respect to the observation hole, and configured to discharge the cooling fluid in a direction different from an observation direction of the endoscope apparatus.

An endoscope system according to an aspect of the present invention includes an endoscope apparatus and a cooling device, and a heat resistant sheath for endoscope including a main body sheath having a substantially tubular shape into which at least a distal end side of an insertion portion of the endoscope apparatus is inserted, and into which a cooling fluid for cooling the insertion portion is supplied by the cooling device, a sheath distal end portion, having a bottomed cylindrical shape with a closed distal end, at which an endoscope distal end portion of the insertion portion inserted into the main body sheath is arranged, and that is connected to a distal end of the main body sheath, an observation hole formed at a middle part of a circumferential side portion of the sheath distal end portion, and configured to expose an observation window provided at a side portion of the endoscope distal end portion to allow observation of an object, and an exhaust hole formed in the circumferential side portion of the sheath distal end portion, on a distal end side with respect to the observation hole, and configured to discharge the cooling fluid in a direction different from an observation direction of the endoscope apparatus.

DETAILED DESCRIPTION OF THE PREFERRED EMBODIMENTS

Figure 1:
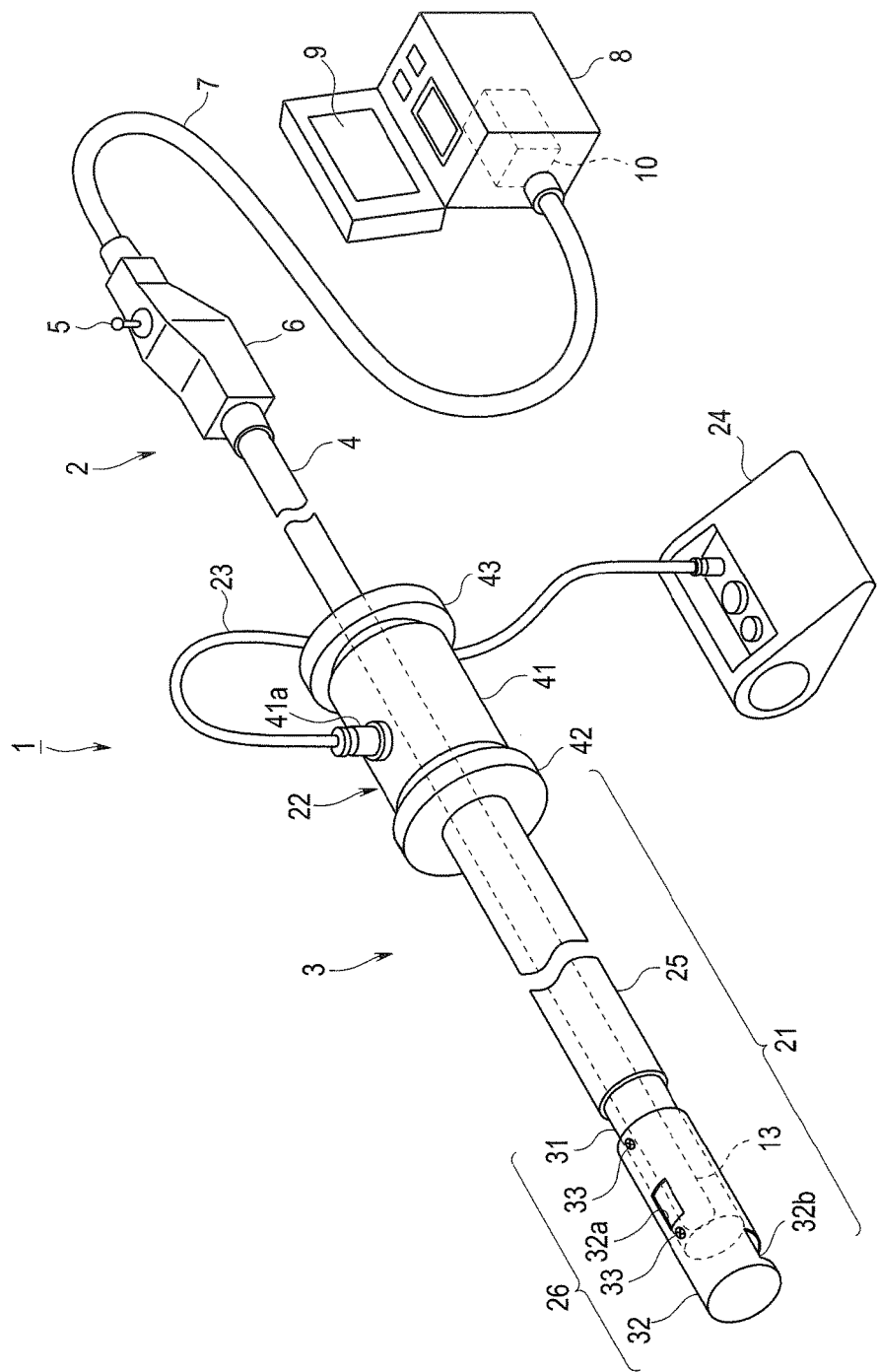
FIG. 1 is a perspective view, according to an aspect of the present invention, showing a configuration of an endoscope system.

Hereinafter, the present invention will be described with reference to the drawings. Note that, in each of the drawings used in the following description, the scale of display of each component is made different such that each component is large enough to be recognized in the drawing. Accordingly, the present invention is not restricted to the modes shown in the drawings with respect to the number of components, the shapes of the components, the proportion of the sizes of the components, and the relative positional relationship of respective components.

Figure 2:
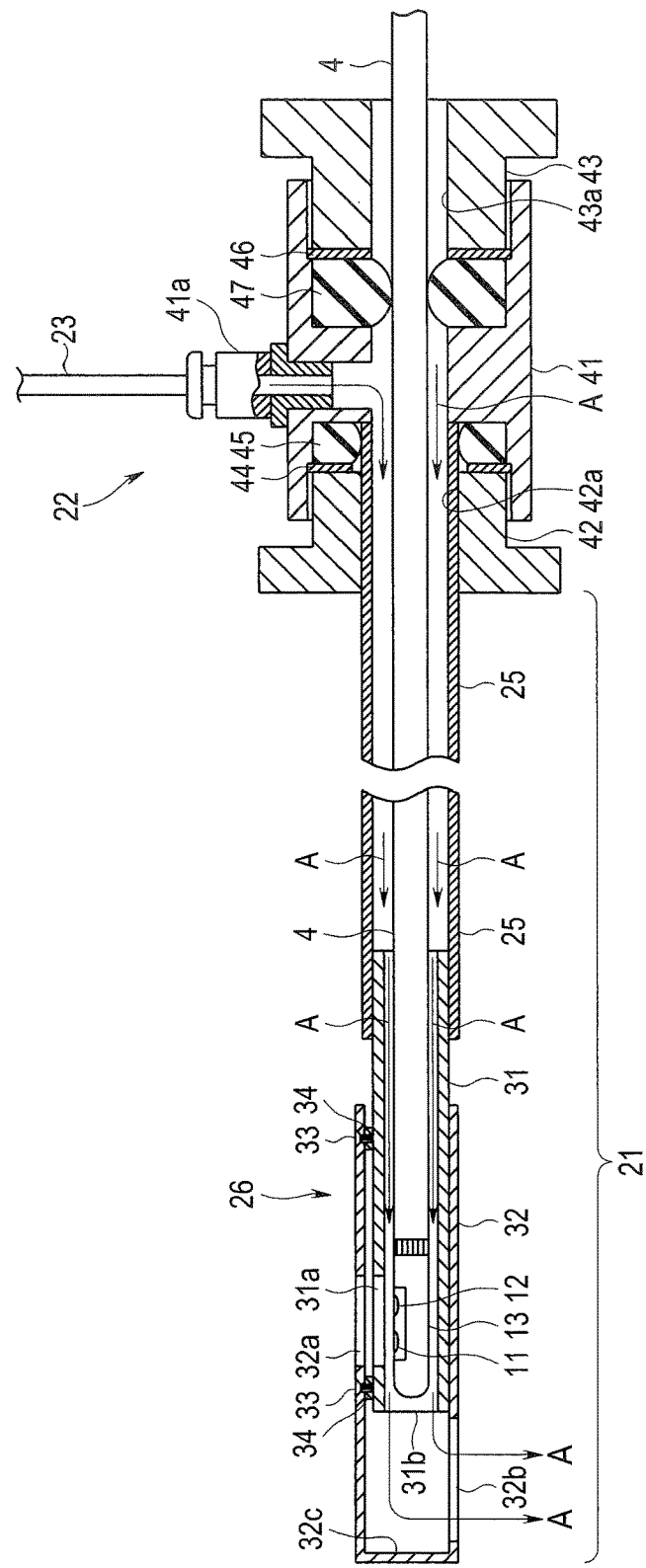
FIG. 2 is a cross-sectional view, according to the aspect of the present invention, showing a configuration of a heat resistant sheath for endoscope into which an insertion portion of an endoscope apparatus is inserted.
Figure 3:
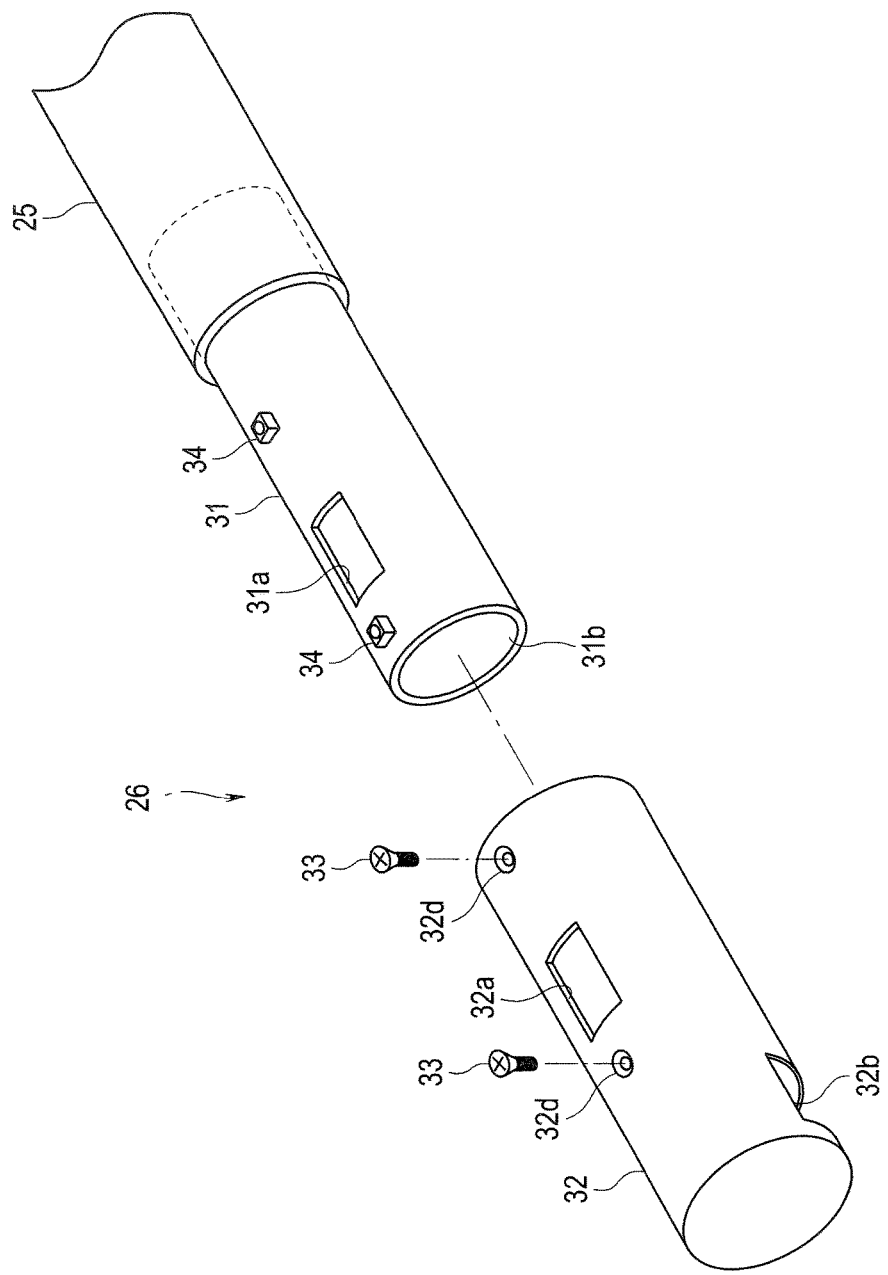
FIG. 3 is an exploded perspective view, according to the aspect of the present invention, showing a configuration of a sheath distal end portion.
Figure 4:
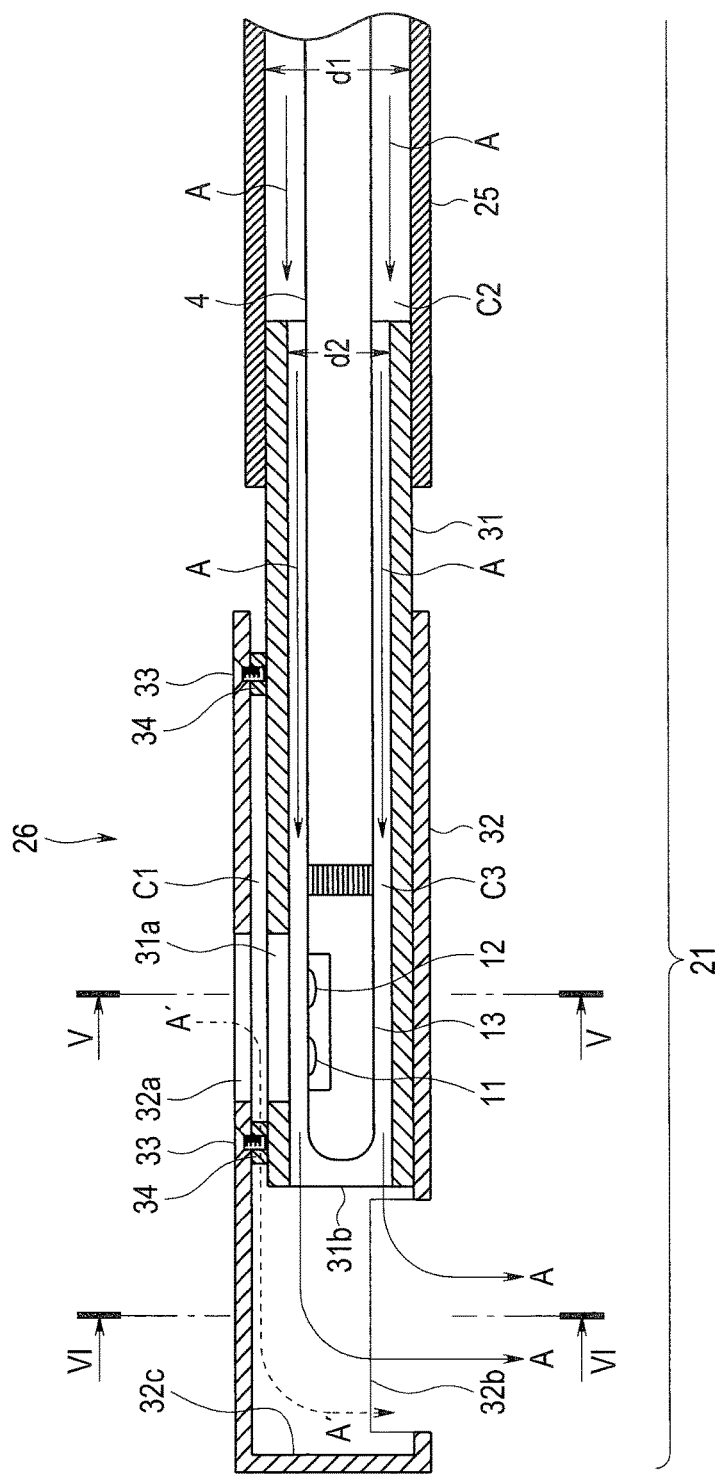
FIG. 4 is a partial cross-sectional view, according to the aspect of the present invention, showing a distal end part of the heat resistant sheath for endoscope into which the insertion portion of the endoscope apparatus is inserted.
Figure 5:
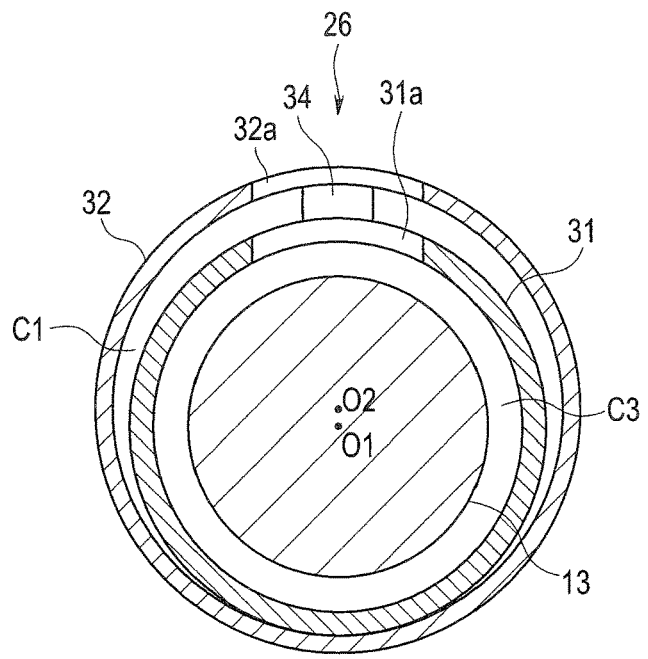
FIG. 5 is a cross-sectional view, according to the aspect of the present invention, along a line V-V in FIG. 4.
Figure 6:
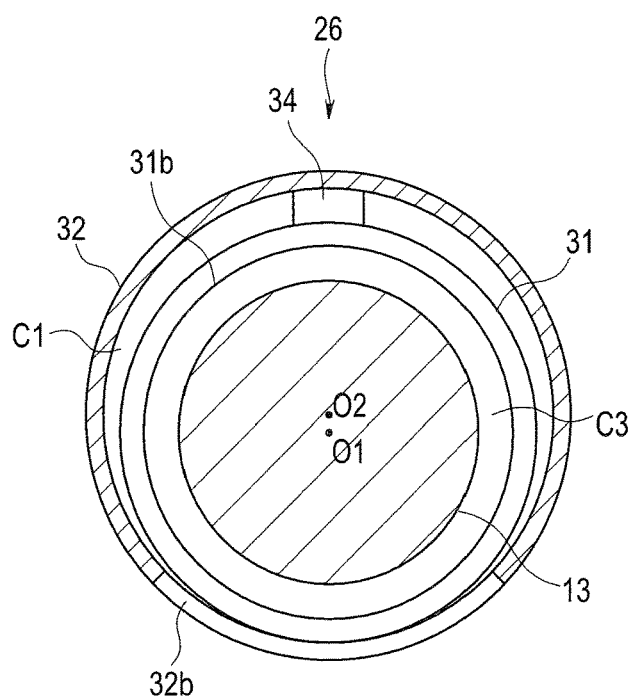
FIG. 6 is a cross-sectional view, according to the aspect of the present invention, along a line VI-VI in FIG. 4.
Figure 7:
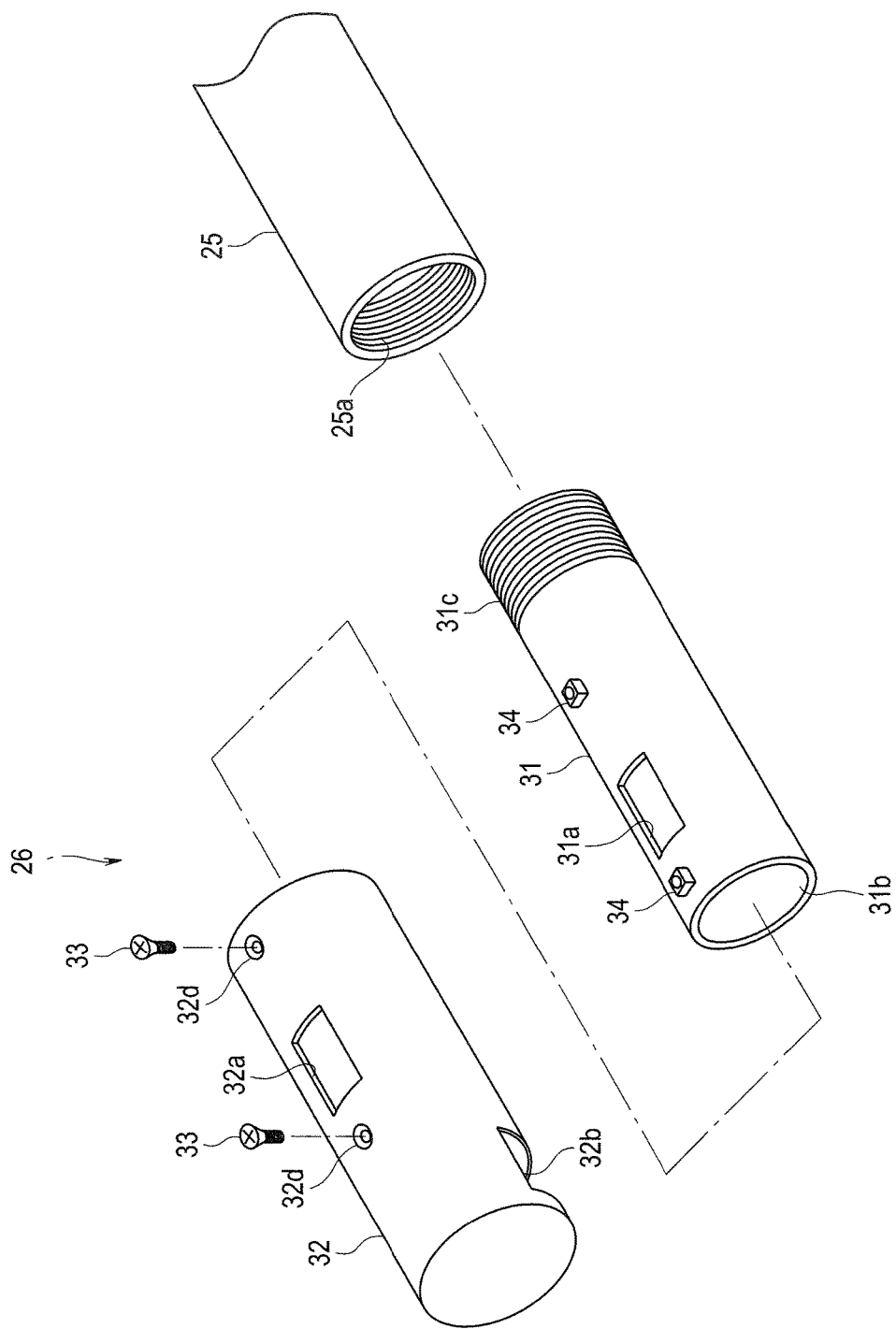
FIG. 7 is an exploded perspective view, according to a first modification of the aspect of the present invention, showing a configuration of a sheath distal end portion.
Figure 8:
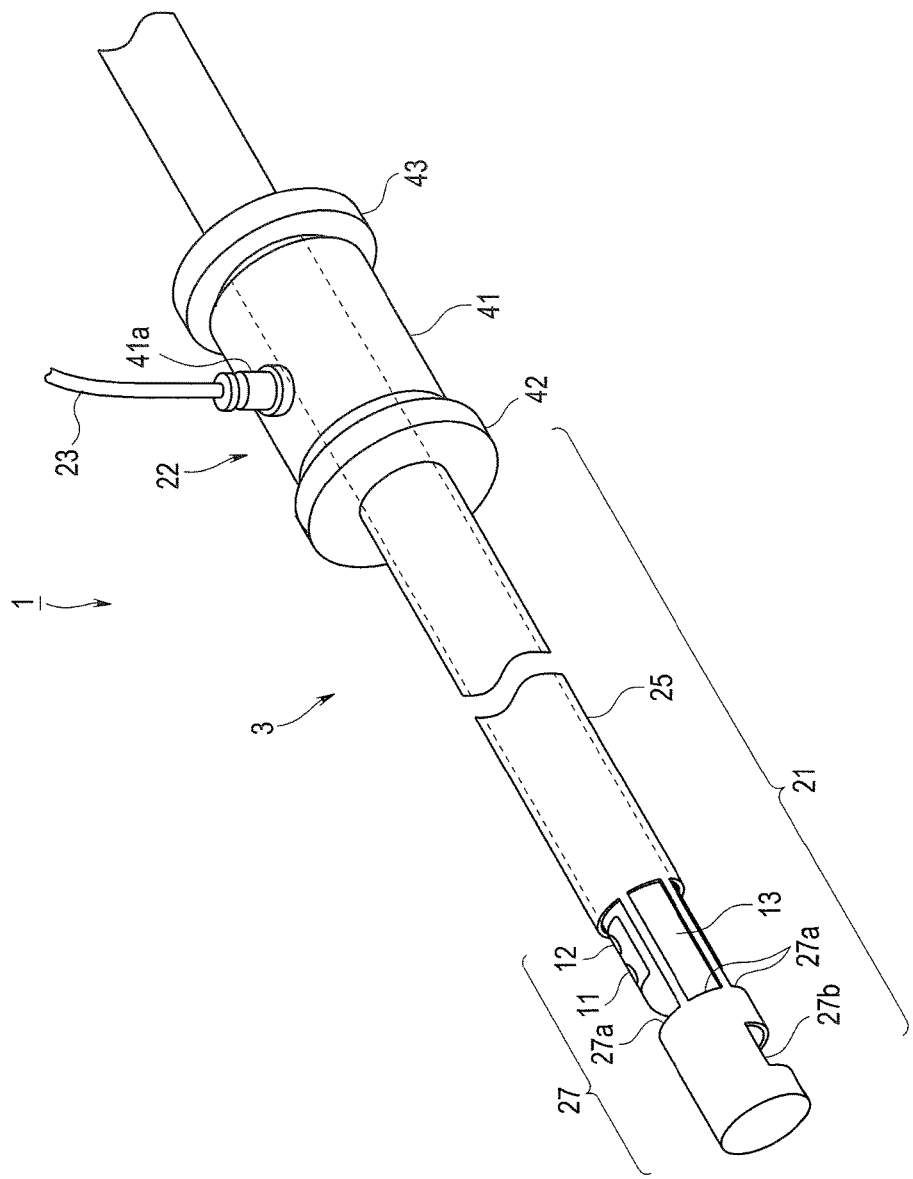
FIG. 8 is a perspective view, according to a second modification of the aspect of the present invention, showing a distal end part of a heat resistant sheath for endoscope into which an insertion portion of an endoscope apparatus is inserted.
Figure 9:
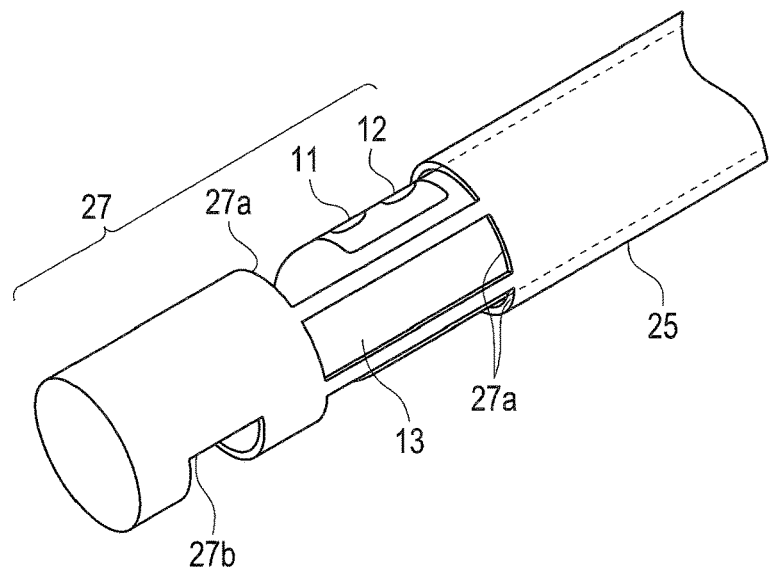
FIG. 9 is a perspective view, according to the second modification of the aspect of the present invention, showing a configuration of a sheath distal end portion.
Figure 10:
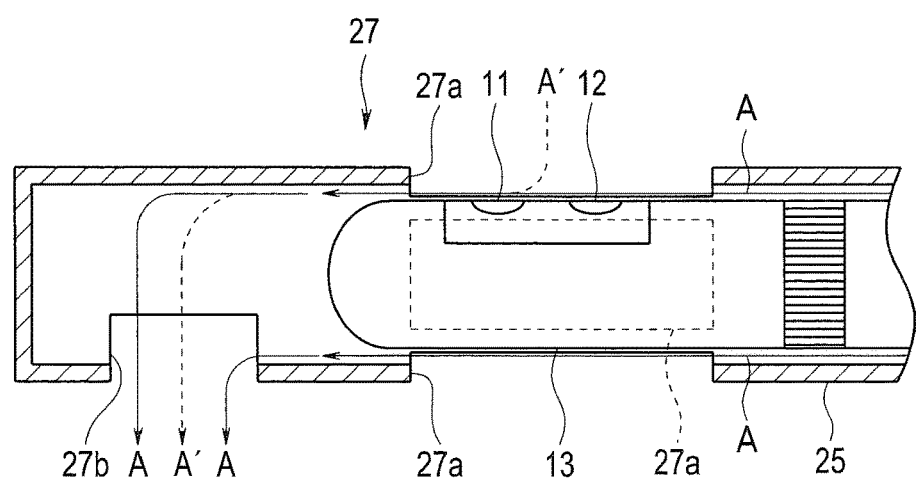
FIG. 10 is a cross-sectional view, according to the second modification of the aspect of the present invention, showing the configuration of the sheath distal end portion.
Figure 11:
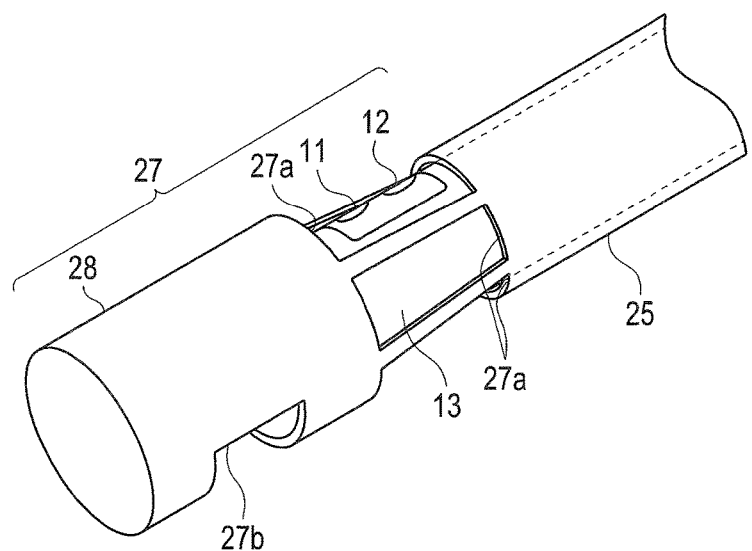
FIG. 11 is a perspective view, according to a third modification of the aspect of the present invention, showing a configuration of a sheath distal end portion.
Figure 12:
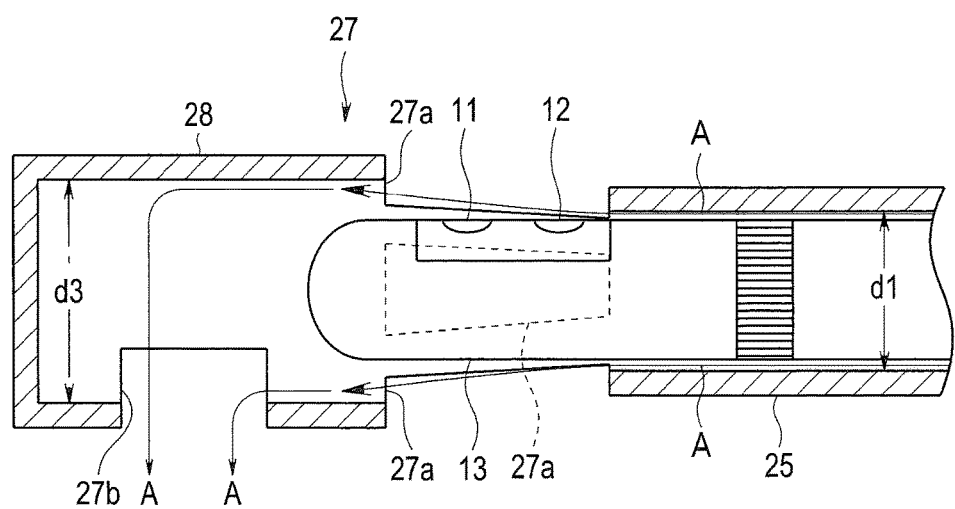
FIG. 12 is a cross-sectional view, according to the third modification of the aspect of the present invention, showing the configuration of the sheath distal end portion.
Figure 13:
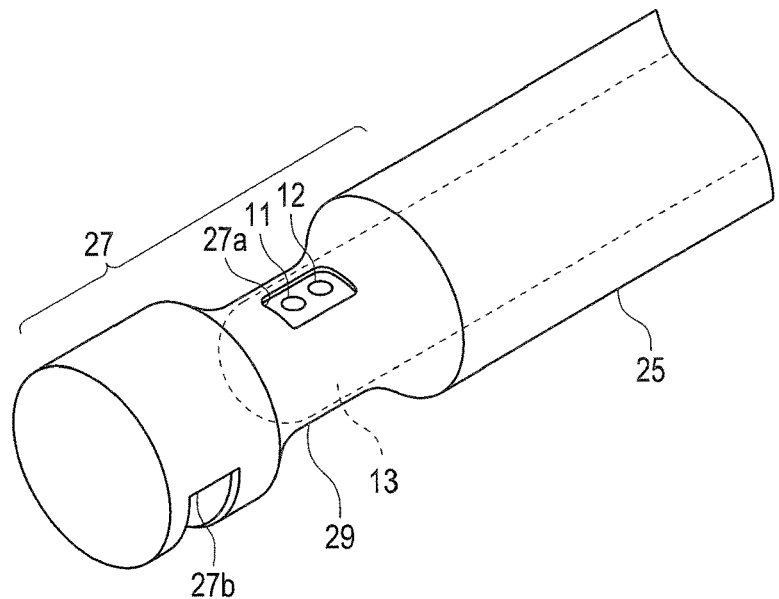
FIG. 13 is a perspective view, according to a fourth modification of the aspect of the present invention, showing a configuration of a sheath distal end portion.
Figure 14:
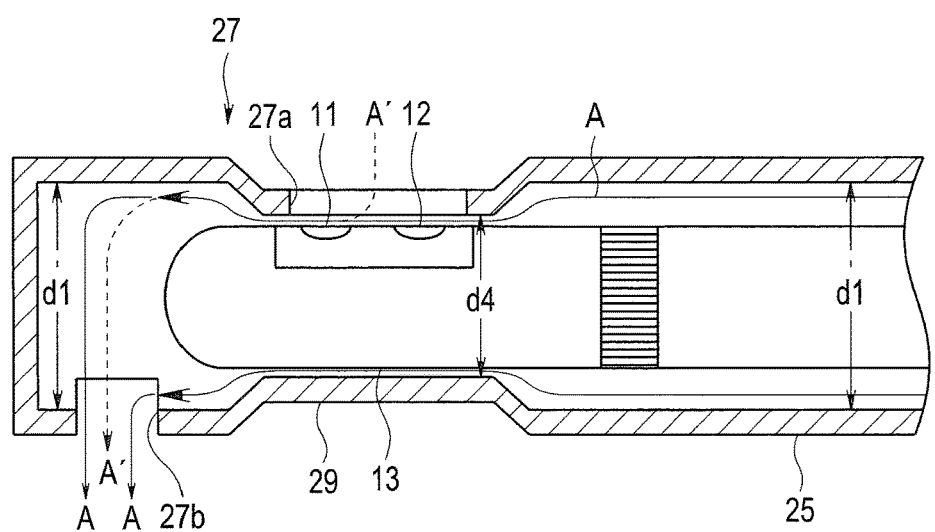
FIG. 14 is a cross-sectional view, according to the fourth modification of the aspect of the present invention, showing the configuration of the sheath distal end portion.
Figure 15:
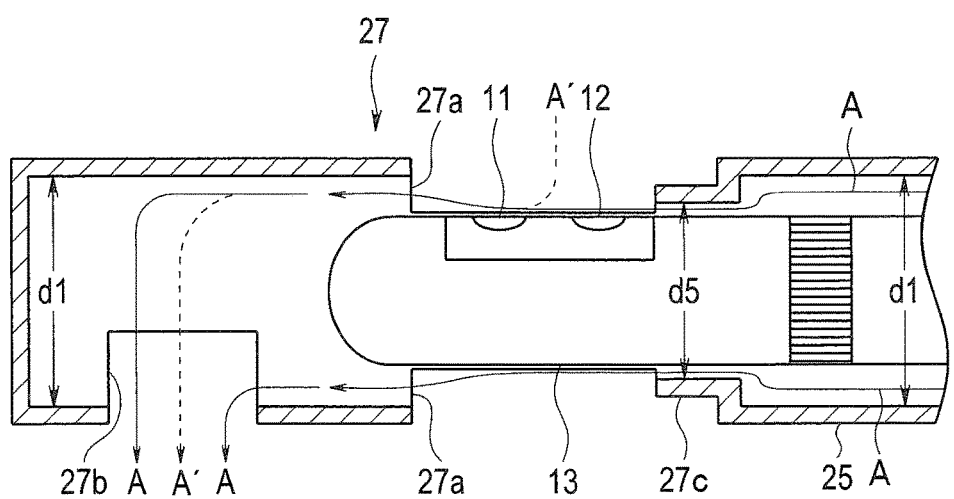
FIG. 15 is a cross-sectional view, according to a fifth modification of the aspect of the present invention, showing a configuration of a sheath distal end portion.
Figure 16:
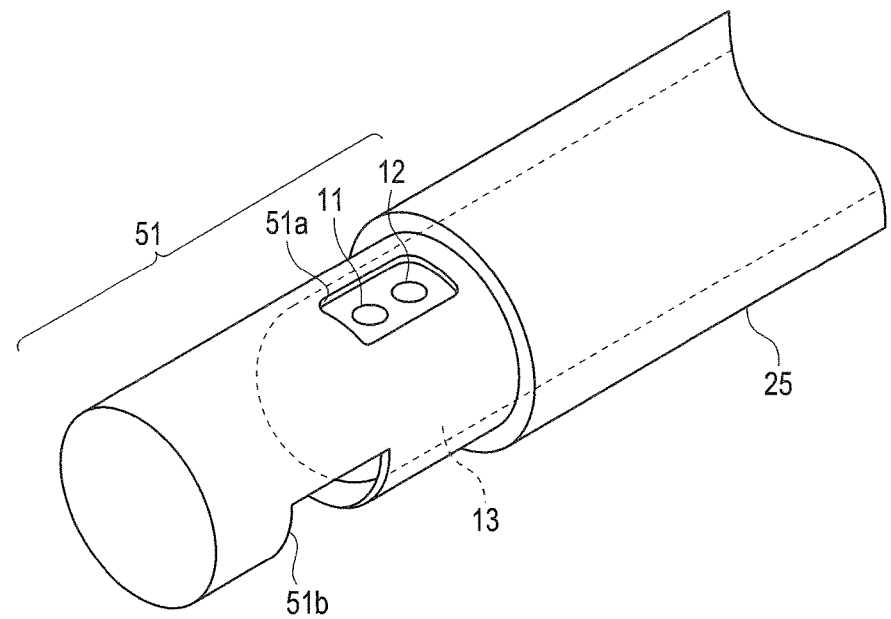
FIG. 16 is a perspective view, according to a sixth modification of the aspect of the present invention, showing a configuration of a sheath distal end portion.
Figure 17:
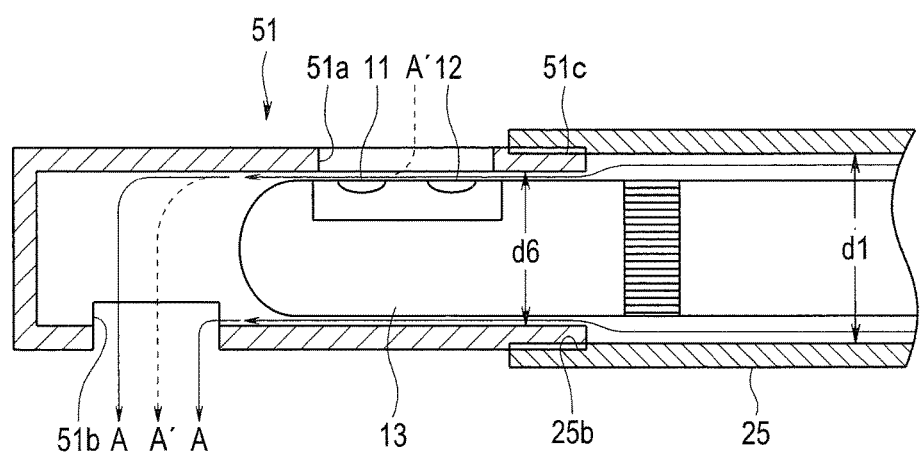
FIG. 17 is a cross-sectional view, according to the sixth modification of the aspect of the present invention, showing the configuration of the sheath distal end portion.
Figure 18:
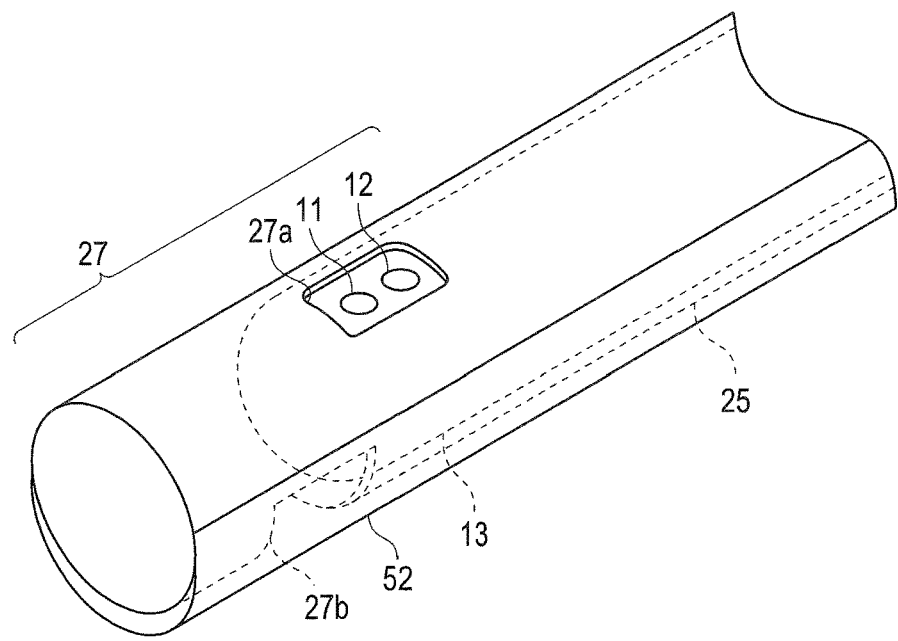
FIG. 18 is a perspective view, according to a seventh modification of the aspect of the present invention, showing a configuration of a sheath distal end portion.
Figure 19:
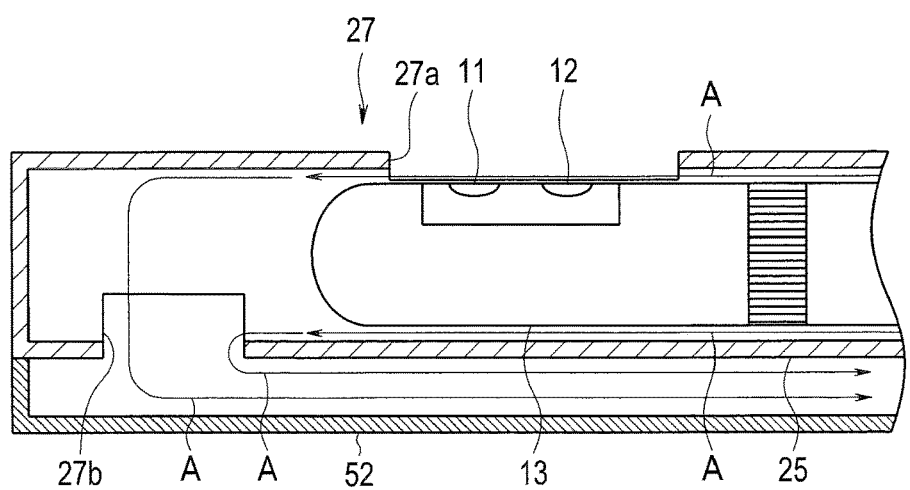
FIG. 19 is a cross-sectional view, according to the seventh modification of the aspect of the present invention, showing the configuration of the sheath distal end portion.
Figure 20:
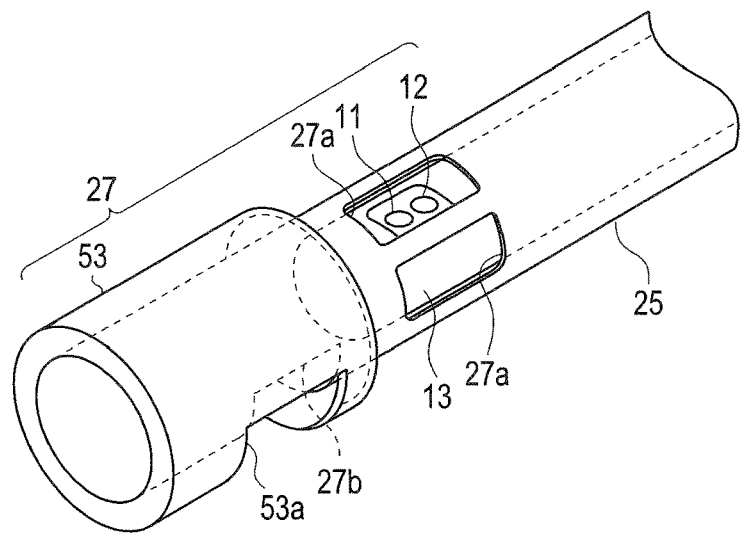
FIG. 20 is a perspective view, according to an eighth modification of the aspect of the present invention, showing a configuration of a sheath distal end portion.
Figure 21:
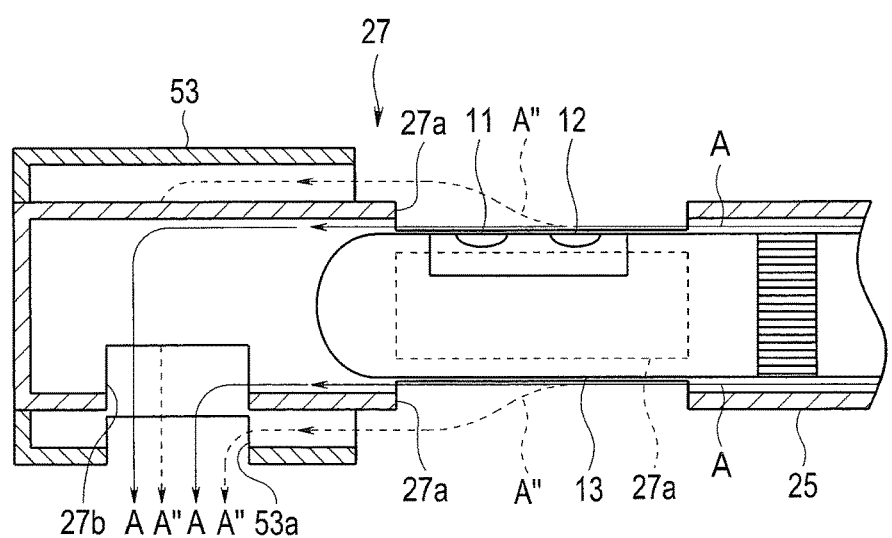
FIG. 21 is a cross-sectional view, according to the eighth modification of the present invention, showing the configuration of the sheath distal end portion.
Figure 22:
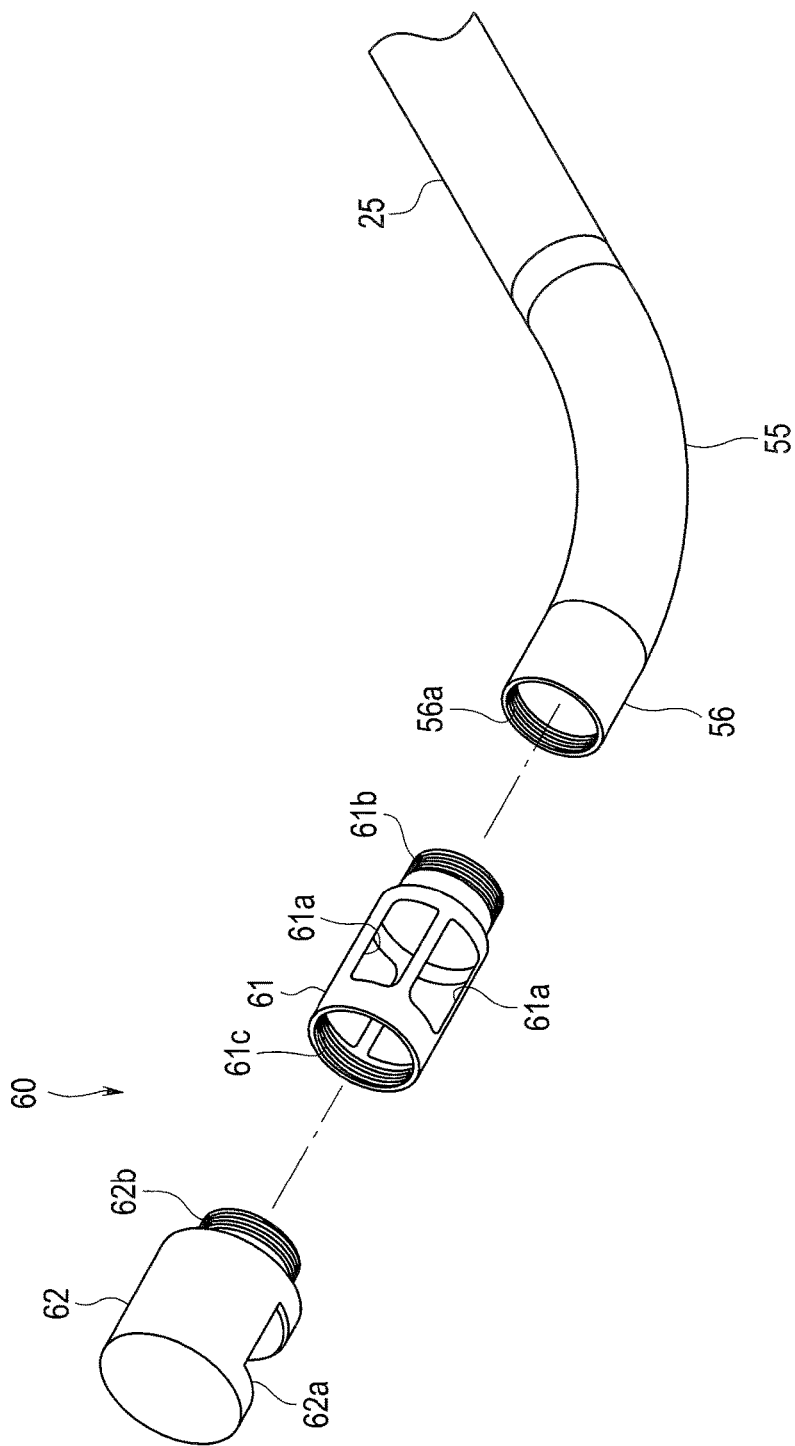
FIG. 22 is an exploded perspective view, according to a ninth modification of the aspect of the present invention, showing a configuration of a heat resistant sheath for endoscope.
Figure 23:
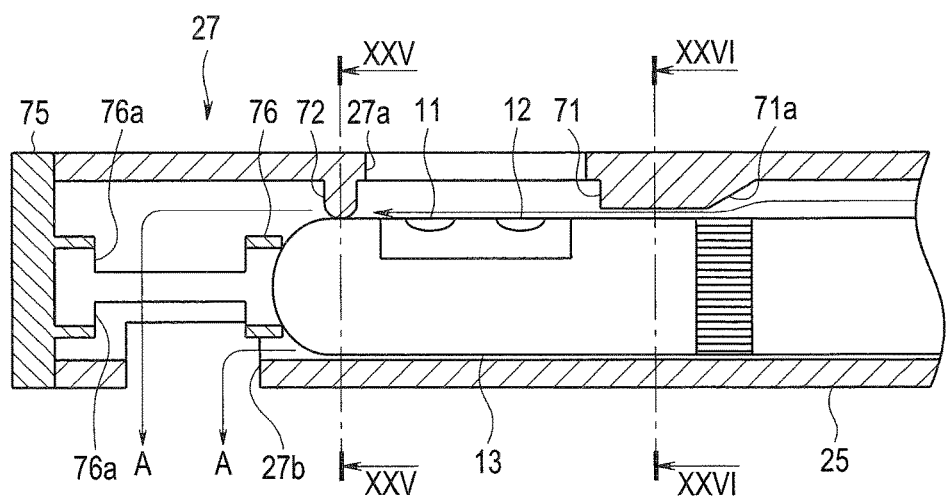
FIG. 23 is a cross-sectional view, according to a tenth modification of the aspect of the present invention, showing a configuration of a sheath distal end portion.
Figure 24:
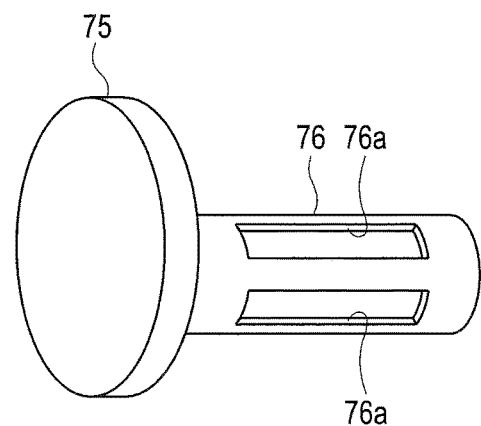
FIG. 24 is a perspective view, according to the tenth modification of the aspect of the present invention, showing a configuration of a cover body.
Figure 25:
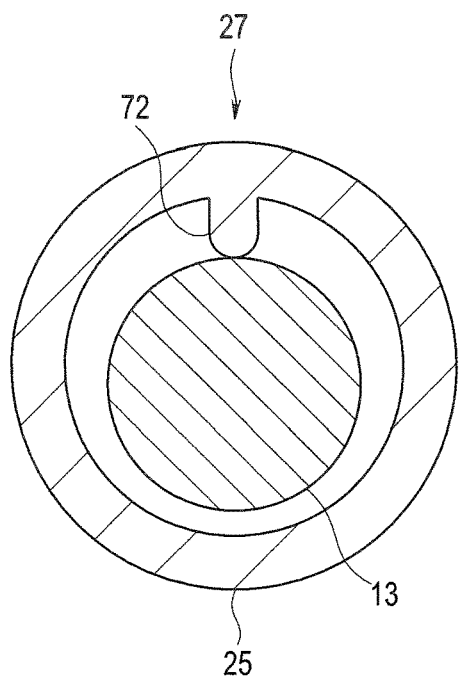
FIG. 25 is a cross-sectional view, according to the tenth modification of the aspect of the present invention, along a line XXV-XXV in FIG. 23.
Figure 26:
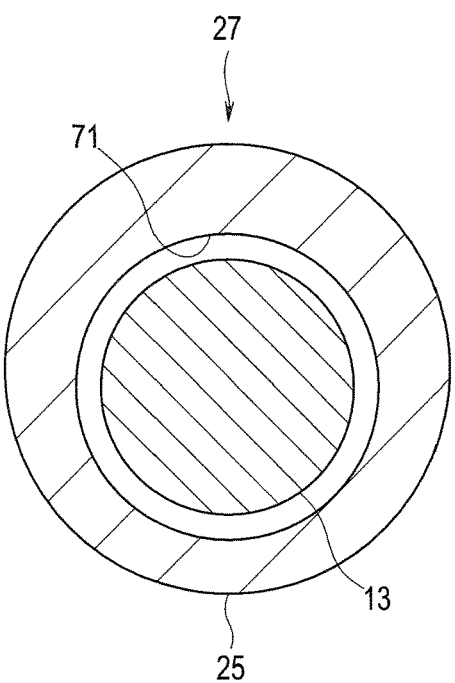
FIG. 26 is a cross-sectional view, according to the tenth modification of the aspect of the present invention, along a line XXVI-XXVI in FIG. 23.

The drawings are according to an aspect of the present invention, and FIG. 1 is a perspective view showing a configuration of an endoscope system, FIG. 2 is a cross-sectional view showing a configuration of a heat resistant sheath for endoscope into which an insertion portion of an endoscope apparatus is inserted, FIG. 3 is an exploded perspective view showing a configuration of a sheath distal end portion, FIG. 4 is a partial cross-sectional view showing a distal end part of the heat resistant sheath for endoscope into which the insertion portion of the endoscope apparatus is inserted, FIG. 5 is a cross-sectional view along a line V-V in FIG. 4, FIG. 6 is a cross-sectional view along a line VI-VI in FIG. 4, FIG. 7 is an exploded perspective view, according to a first modification, showing a configuration of a sheath distal end portion, FIG. 8 is a perspective view, according to a second modification, showing a distal end part of a heat resistant sheath for endoscope into which an insertion portion of an endoscope apparatus is inserted, FIG. 9 is a perspective view, according to the second modification, showing a configuration of a sheath distal end portion, FIG. 10 is a cross-sectional view, according to the second modification, showing the configuration of the sheath distal end portion, FIG. 11 is a perspective view, according to a third modification, showing a configuration of a sheath distal end portion, FIG. 12 is a cross-sectional view, according to the third modification, showing the configuration of the sheath distal end portion, FIG. 13 is a perspective view, according to a fourth modification, showing a configuration of a sheath distal end portion, FIG. 14 is a cross-sectional view, according to the fourth modification, showing the configuration of the sheath distal end portion, FIG. 15 is a cross-sectional view, according to a fifth modification, showing a configuration of a sheath distal end portion, FIG. 16 is a perspective view, according to a sixth modification, showing a configuration of a sheath distal end portion, FIG. 17 is a cross-sectional view, according to the sixth modification, showing the configuration of the sheath distal end portion, FIG. 18 is a perspective view, according to a seventh modification, showing a configuration of a sheath distal end portion, FIG. 19 is a cross-sectional view, according to the seventh modification, showing the configuration of the sheath distal end portion, FIG. 20 is a perspective view, according to an eighth modification, showing a configuration of a sheath distal end portion, FIG. 21 is a cross-sectional view, according to the eighth modification, showing the configuration of the sheath distal end portion, FIG. 22 is an exploded perspective view, according to a ninth modification, showing a configuration of a heat resistant sheath for endoscope, FIG. 23 is a cross-sectional view, according to a tenth modification, showing a configuration of a sheath distal end portion, FIG. 24 is a perspective view, according to the tenth modification, showing a configuration of a cover body, FIG. 25 is a cross-sectional view, according to the tenth modification, along a line XXV-XXV in FIG. 23, and FIG. 26 is a cross-sectional view, according to the tenth modification, along a line XXVI-XXVI in FIG. 23.

As shown in FIGS. 1 and 2, an endoscope system 1 according to the present embodiment includes an endoscope apparatus 2, and a heat resistant sheath 3 for endoscope, which is an endoscope guide sheath.

The endoscope apparatus 2 includes an elongated and flexible insertion portion 4, which is to be inserted into an object, an operation section 6 provided with a joystick 5 configured to perform an operation of bending the insertion portion 4, a composite cable 7 extending from a proximal end of the operation section 6, and a main body section 8 to which the composite cable 7 is connected in a detachable/attachable manner.

The insertion portion 4 is provided at a circumferential side portion of an endoscope distal end portion 13 including an illumination window 11 and an observation window 12. That is, the endoscope apparatus 2 of the present embodiment is a side-view type endoscope apparatus.

The illumination window 11 is provided with an illumination optical system. The illumination optical system directs illumination light transmitted by a light guide, not shown, from the illumination window 11 to an object. The illumination light is emitted by a light source 10 provided to the main body section 8.

An observation optical system is provided to the observation window 12 provided to the endoscope distal end portion 13 of the insertion portion 4. Also, an image pickup apparatus (not shown) including an image sensor, such as a CCD or CMOS, configured to detect an object image formed by the observation optical system is provided inside the endoscope distal end portion 13.

A display section 9, such as an LCD, is disposed at the main body section 8, and an endoscopic image picked up by the image sensor of the image pickup apparatus is displayed on the display section 9.

Note that the endoscope apparatus 2 is configured in the same manner as in the past, and description of other details is omitted.

A configuration of the heat resistant sheath 3 for endoscope according to the present embodiment will be described below in detail.

As shown in FIGS. 1 and 2, the heat resistant sheath 3 for endoscope includes a guide main body 21 into which a distal end side of the insertion portion 4 of the endoscope apparatus 2 is inserted, and a proximal end pipe sleeve 22 connected to a proximal end of the guide main body 21.

The heat resistant sheath 3 for endoscope has an air hose 23 connected to the proximal end pipe sleeve 22, and compressed air as a cooling fluid is supplied through the air hose 23 from an air compressor 24 serving as a cooling device, which is fluid supply means.

The guide main body 21 includes a main body sheath 25, which is a heat-resistant rigid metal tube, and a sheath distal end portion 26 disposed on a distal end of the main body sheath 25.

Note that, as a structure having higher heat resistance and heat insulation properties, the main body sheath 25 may have a multilayer tube structure according to which a metal tube is covered with a heat insulating sheath formed of urethane resin, and a heat resistant sheath for endoscope formed of foamed fluorocarbon resin or silicone resin is externally attached to the heat insulating sheath, for example.

Furthermore, the main body sheath 25 is not limited to be a rigid metal tube, and may be a flexible tube body formed of fluorocarbon resin, polyimide, PEEK, urethane resin or the like so as to have flexibility.

As shown in FIGS. 3 and 4, the sheath distal end portion 26 includes a first cylindrical body 31 as an inner cylinder, which is a rigid metal tube fitted into and connected to the distal end of the main body sheath 25, and a second cylindrical body 32 as an outer cylinder, which is a rigid metal tube disposed over the first cylindrical body 31.

The first cylindrical body 31 is a tubular member with a diameter smaller than that of the main body sheath 25, the first cylindrical body 31 having an observation opening portion 31a as an observation hole of the endoscope apparatus 2 formed on the distal end side of a circumferential side portion, and including a distal end opening portion 31b.

Furthermore, the first cylindrical body 31 includes two protruding portions 34, for fastening screws, to which flat head screws 33 configured to fix the second cylindrical body 32 at outer circumferential portions in a front-back direction of the observation opening portion 31a are attached threadedly.

The second cylindrical body 32 is a tubular member having a bottomed cylindrical shape with a closed distal end, the second cylindrical body 32 having an outer diameter larger than that of the first cylindrical body 31, and including an observation opening portion 32a forming an observation hole formed at a middle part of a circumferential side portion and an exhaust opening portion 32b as an exhaust hole formed at the circumferential side portion, at a position point symmetrical to the observation opening portion 32a with respect to any point on a central axis of the second cylindrical body 32.

Note that the exhaust opening portion 32b is formed on the distal end side with respect to the observation opening portion 32a, and the opening area of the exhaust opening portion 32b is set larger than that of the observation opening portion 32a.

Furthermore, the opening area of the exhaust opening portion 32b is set equal to or larger than the opening area of the distal end opening portion 31b. By performing setting in the above manner, air may be smoothly discharged from the exhaust opening portion 32b.

Moreover, the observation opening portion 31a of the first cylindrical body 31 and the observation opening portion 32a of the second cylindrical body 32 have approximately the same opening area.

Note that, in accordance with the view angle of the endoscope apparatus 2, the observation opening portion 32a of the second cylindrical body 32 on the outer side of the sheath distal end portion 26 preferably has an opening area that is slightly larger than that of the observation opening portion 31a of the first cylindrical body 31 on the inner side.

Furthermore, the respective observation opening portions 31a, 32a are fixed in an overlapping manner by inserting the second cylindrical body 32 over the first cylindrical body 31, where the two flat head screws 33 are threadedly attached to the respective protruding portions 34.

Moreover, the second cylindrical body 32 has flat head screw holes 32d formed at outer circumferential portions in a front-back direction of the opening portion 32a so that head portions of the flat head screws 33 do not protrude from an outer surface.

Note that, as shown in FIGS. 5 and 6, the first cylindrical body 31 and the second cylindrical body 32 are eccentrically fixed with respective centers 01, 02 at shifted positions.

That is, the second cylindrical body 32 is fixed in a state where an inner circumferential surface is in contact with surfaces of the protruding portions 34, and the inner circumferential surface opposite the protruding portions 34 is in contact with an outer circumferential surface of the first cylindrical body 31, and is eccentric along the direction of height of the protruding portions 34. Accordingly, a clearance C1 is formed between the outer circumferential surface of the first cylindrical body 31 and the inner circumferential surface of the second cylindrical body 32.

Note that, as a structure having higher heat resistance and heat insulation properties, the sheath distal end portion 26 may have a multilayer tube structure according to which the first cylindrical body 31 and the second cylindrical body 32, which are metal tubes, are covered with a heat insulating sheath formed of urethane resin, and a heat resistant sheath for endoscope formed of foamed fluorocarbon resin or silicone resin is externally attached to the heat insulating sheath, for example.

Referring back to FIG. 2, the proximal end pipe sleeve 22 to which a proximal end of the main body sheath 25 is connected is a substantially tubular member, and includes a substantially cylindrical pipe sleeve main body portion 41 provided with a supply port 41a to which the air hose 23 is connected, a first fixing member 42 threadedly attached to a distal end side of the pipe sleeve main body portion 41, and a second fixing member 43 threadedly attached to a proximal end side of the pipe sleeve main body portion 41.

Note that compressed air A from the air compressor 24 is supplied through the air hose 23 to the supply port 41a provided to the pipe sleeve main body portion 41.

The first fixing member 42 is a substantially columnar member including a through hole 42a through which a proximal end part of the main body sheath 25 is inserted, and having an outward flange formed on a distal end side.

Inside a thread connection portion of the pipe sleeve main body portion 41 to which the first fixing member 42 is threadedly attached, a substantially annular washer 44 in contact with an end face of the first fixing member 42 and a packing 45 formed of an elastic material are provided in this order from the distal end side.

The packing 45 is an annular member formed of silicone rubber, for example, and the inner diameter of a hole portion is set substantially equal to the outer diameter of the main body sheath 25. When the first fixing member 42 is fastened into the pipe sleeve main body portion 41, the packing 45 is crushed and is elastically deformed to expand to the inner circumferential surface side.

The main body sheath 25 is thereby fixed to the proximal end pipe sleeve 22 in a state where the packing 45 is in close contact with the outer circumferential surface of a proximal end part and the airtightness is maintained.

The second fixing member 43 is a substantially columnar member including a through hole 43a through which the insertion portion 4 is inserted, and having an outward flange formed on a proximal end side.

Inside a thread connection portion of the pipe sleeve main body portion 41 to which the second fixing member 43 is threadedly attached, a substantially annular washer 46 in contact with an end face of the second fixing member 43 and a packing 47 formed of an elastic material are provided in this order from the proximal end side.

The packing 47 is an annular member formed of silicone rubber, for example, and the inner diameter of a hole portion is set substantially equal to the outer diameter of the insertion portion 4 of the endoscope apparatus 2. When the second fixing member 43 is fastened into the pipe sleeve main body portion 41, the packing 47 is crushed and is elastically deformed to expand to the inner circumferential surface side.

The insertion portion 4 of the endoscope apparatus 2 inserted into the proximal end pipe sleeve 22 is thereby fixed to the proximal end pipe sleeve 22 in a state where the packing 47 is in close contact with the outer circumferential surface and airtightness is maintained. Note that the packing 47 is very flexible so as to conform to the shape and size of the insertion portion 4 of the endoscope apparatus 2.

Next, an action of the endoscope system 1 of the present embodiment configured in the above manner will be described.

When an examination, such as combustion testing of a fuel in an internal combustion engine, combustion testing of combustible materials in an incinerator, or melting testing of solder in a reflow furnace, is to be performed in a high temperature environment, the endoscope system 1 first has the guide main body 21 of the heat resistant sheath 3 for endoscope inserted into an object from the sheath distal end portion 26 side.

Next, the insertion portion 4 of the endoscope apparatus 2 is inserted into the guide main body 21 from the proximal end side of the proximal end pipe sleeve 22 of the heat resistant sheath 3 for endoscope.

Then, based on an endoscopic image displayed on the display section 9 of the main body section 8 shown in FIG. 1, the illumination window 11 and the observation window 12 of the endoscope distal end portion 13 of the insertion portion 4 are adjusted to be at positions where the illumination window 11 and the observation window 12 are exposed from the respective observation opening portions 31a, 32a of the sheath distal end portion 26, and the insertion portion 4 is fixed by the fastening of the second fixing member 43 of the proximal end pipe sleeve 22.

That is, the endoscope distal end portion 13 is arranged inside the sheath distal end portion 26 in such a way that the illumination window 11 and the observation window 12 coincide with the respective observation opening portions 31a, 32a of the sheath distal end portion 26 so as to allow observation of the object through each of the observation opening portions 31a, 32a.

Here, the air compressor 24 shown in FIG. 1 is driven, and the compressed air A (see FIG. 2) as cooling air is supplied from the air hose 23 into the guide main body 21 through the supply port 41a of the proximal end pipe sleeve 22.

Here, as shown in FIG. 2, by causing the packing 47 to be in close contact with the proximal end of the insertion portion 4 and maintaining airtightness, the compressed air A from the air compressor 24 is fed to a distal end side of the guide main body 21 without being discharged to a proximal end side.

In the above state, the position of the insertion portion 4 is adjusted together with that of the heat resistant sheath 3 for endoscope based on an endoscopic image displayed on the display section 9 of the main body section 8 shown in FIG. 1 so as to allow observation of an examination target part inside the object.

Moreover, the compressed air A from the air compressor 24 is constantly supplied into the guide main body 21 of the heat resistant sheath 3 for endoscope during observation by the endoscope system 1, and the insertion portion 4 is cooled by the compressed air A fed into the guide main body 21.

Note that because an inner diameter d2 of the first cylindrical body 31 of the sheath distal end portion 26 is smaller than an inner diameter d1 of the main body sheath 25, as shown in FIG. 4, the flow velocity of the compressed air A fed from the main body sheath 25 of the guide main body 21 to the sheath distal end portion 26 is increased in the first cylindrical body 31 compared to the flow velocity in the main body sheath 25; that is, the flow velocity is increased due to the so-called Venturi effect.

That is, because the cross-sectional area of a clearance C3 formed between an inner surface of the first cylindrical body 31 and an outer surface of the insertion portion 4 is smaller than the cross-sectional area of a clearance C2 formed between an inner surface of the main body sheath 25 and the outer surface of the insertion portion 4, the flow velocity of the compressed air A fed from inside the main body sheath 25 into the first cylindrical body 31 is increased.

Here, at the sheath distal end portion 26, the compressed air A fed into the first cylindrical body 31 blows against a closed distal end wall surface 32c of the second cylindrical body 32, for example, and is discharged from the exhaust opening portion 32b provided on the distal end side with respect to the observation opening portion 31a of the first cylindrical body 31 and the observation opening portion 32a of the second cylindrical body 32.

Note that the compressed air A is constantly fed from the main body sheath 25, and thus the compressed air A is discharged from the exhaust opening portion 32b of the second cylindrical body 32 without flowing backward inside the sheath distal end portion 26.

When the flow velocity of the compressed air A inside the first cylindrical body 31 is increased in the above state due to the so-called Venturi effect, a phenomenon occurs, at the observation opening portion 31a of the first cylindrical body 31 and the observation opening portion 32a of the second cylindrical body 32 provided on the proximal end side with respect to the exhaust opening portion 32b, where outside air A' near the observation opening portion 32a of the second cylindrical body 32 is slightly drawn into the sheath distal end portion 26.

Note that the outside air A' drawn in from the observation opening portion 32a of the second cylindrical body 32 is mainly drawn into the clearance C1 formed between the outer circumferential surface of the first cylindrical body 31 and the inner circumferential surface of the second cylindrical body 32, and is discharged from the exhaust opening portion 32b of the second cylindrical body 32 together with the compressed air A.

Slight negative pressure is caused by the phenomenon at each of the observation opening portions 31a, 32a in the opposite direction from the observation direction of the endoscope apparatus 2.

Accordingly, the compressed air A fed to the sheath distal end portion 26 is hardly discharged in the observation direction of the endoscope apparatus 2 from the observation opening portion 31a of the first cylindrical body 31 and the observation opening portion 32a of the second cylindrical body 32 disposed in a manner allowing the illumination window 11 and the observation window 12 of the endoscope apparatus 2 to be exposed, and is discharged from the exhaust opening portion 32b on the opposite side from each of the observation opening portions 31a, 32a.

Note that because the inner diameter of the second cylindrical body 32 is set larger than the inner diameter of the first cylindrical body 31, and the clearance C1 is formed, air spreading from the first cylindrical body 31 toward the observation opening portion 31a is drawn into the clearance C1 even if suction of air from the observation opening portion 32a and the observation opening portion 31a is interrupted for some reason. As a result, an effect of making leakage of air from the observation opening portion 32a difficult is obtained.

That is, the compressed air A fed to the sheath distal end portion 26 is discharged to the opposite side from the observation direction of the object by the endoscope apparatus 2. Also, here, the exhaust opening portion 32b is formed at a position point symmetrical to the observation opening portion 32a with respect to any point on the central axis of the second cylindrical body 32 of the sheath distal end portion 26, but this is not restrictive, and the position where the exhaust opening portion 32b is formed may be any position of the second cylindrical body 32 so long as the discharge direction of the compressed air A is different from the direction of observation of an object by the endoscope apparatus 2 through each of the observation opening portions 31a, 32a.

That is, the exhaust opening portion 32b may be formed at a position different from the observation opening portion 32a, on the circumferential side portion of the second cylindrical body 32. Also, the exhaust opening portion 32b may be formed at a position separate from the observation opening portion 32a by 90 degrees or more on the circumferential side portion of the second cylindrical body 32. Moreover, as shown in FIG. 4, the exhaust opening portion 32b may be formed at a position separate from the observation opening portion 32a by 180 degrees or more on the circumferential side portion of the second cylindrical body 32.

Note that, in the case described above, the guide main body 21 of the heat resistant sheath 3 for endoscope is first inserted into the object, and then the insertion portion 4 is inserted into the guide main body 21 while driving the air compressor 24, but this is not restrictive, and the guide main body 21 and the insertion portion 4 may be integrally inserted into the object, after the insertion portion 4 is previously inserted into the guide main body 21, while driving the air compressor 24.

As described above, according to the endoscope system 1 of the present embodiment, at the time of observation in a high temperature environment, such as at the time of combustion testing of a fuel in an internal combustion engine, combustion testing of combustible materials in an incinerator, or melting testing of solder in a reflow furnace, the insertion portion 4 of the endoscope apparatus 2 is cooled by the compressed air A from the air compressor 24 fed into the clearances C2, C3 as cooling channels formed between the guide main body 21 of the heat resistant sheath 3 for endoscope and the insertion portion 4.

The endoscope system 1 may conduct accurate examination without greatly changing the environment of the examination target because the compressed air A is hardly discharged in the direction of the examination part being observed by the endoscope apparatus 2 through the observation opening portion 31a of the first cylindrical body 31 and the observation opening portion 32a of the second cylindrical body 32.

Furthermore, the heat resistant sheath 3 for endoscope of the present embodiment is not configured to circulate the compressed air A as the cooling air by providing a cover glass, as in a conventional case, and thus a cover glass surface is not clouded with condensation and no flare (halation) is caused by the illumination light from the endoscope apparatus 2 or by the light of fire at the time of combustion testing, and the examination part may be clearly observed, and the testing efficiency is not reduced.

Note that because the heat resistant sheath 3 for endoscope is not provided with a cover glass, an illumination device for preventing flare (halation) by the illumination light from the endoscope apparatus 2 does not have to be separately provided, and an examination part may be observed by illumination by the endoscope apparatus 2.

As described above, the heat resistant sheath 3 for endoscope according to the present embodiment and the endoscope system including the heat resistant sheath 3 for endoscope are configured in a manner allowing examination inside a high-temperature object without changing the environment of the examination target as much as possible, and in a manner allowing clear observation and preventing reduction in the examination efficiency.

First Modification

Note that the sheath distal end portion 26 of the heat resistant sheath 3 for endoscope may have a male screw portion 31c formed at a proximal end portion such that the first cylindrical body 31 may be threadedly attached/detached to/from a female screw portion 25a formed at a distal end part of the main body sheath 25, as shown in FIG. 7, for example.

According to such a configuration, the heat resistant sheath 3 for endoscope may allow selection and exchange of the sheath distal end portion 26 including the observation opening portions 31a, 32a according to different types of endoscope apparatuses 2.

Second Modification

As shown in FIGS. 8 and 9, the heat resistant sheath 3 for endoscope in the present case uses a bottomed cylindrical main body sheath 25 with a closed distal end, instead of the structure of the sheath distal end portion 26 of the guide main body 21 described above, and includes a plurality of, such as four, rectangular observation opening portions 27a as observation holes formed around the outer circumference of the sheath distal end portion 27 of the main body sheath 25, and an exhaust opening portion 27b as an exhaust hole formed on the distal end side with respect to the observation opening portions 27a.

Also according to such a configuration, at the time of observation by the endoscope system 1, the heat resistant sheath 3 for endoscope has the compressed air A for cooling the insertion portion 4 supplied into the guide main body 21 of the heat resistant sheath 3 for endoscope from the air compressor 24, and the compressed air A fed from the main body sheath 25 of the guide main body 21 to the sheath distal end portion 27 is discharged from the exhaust opening portion 27b formed in the sheath distal end portion 27, as shown in FIG. 10.

Note that also with the heat resistant sheath 3 for endoscope in the present case, the flow velocity of the compressed air A which is fed is increased at the sheath distal end portion 27 due to the so-called Venturi effect, and the compressed air A is discharged mainly from the exhaust opening portion 27b provided on the distal end side with respect to the plurality of observation opening portions 27a.

Third Modification

As shown in FIGS. 11 and 12, the heat resistant sheath 3 for endoscope in the present case is provided, in addition to the configuration of the second modification described above, with an enlarged diameter portion 28, which is the sheath distal end portion 27 on the distal end side with respect to the plurality of observation opening portions 27a, the diameter of the enlarged diameter portion 28 being larger than the outer diameter of the main body sheath 25. That is, as shown in FIG. 12, the enlarged diameter portion 28 has an inner diameter d3 larger than the inner diameter d1 of the main body sheath 25.

According to the heat resistant sheath 3 for endoscope having such a configuration, at the time of observation by the endoscope system 1, even if the compressed air A from the air compressor 24 for cooling the insertion portion 4 spreads outside the main body sheath 25 of the guide main body 21 at the time of passing through the plurality of observation opening portions 27a, the compressed air A flows into the enlarged diameter portion 28 provided on the distal end side with respect to the plurality of observation opening portions 27a and is discharged mainly from the exhaust opening portion 27b.

Fourth Modification

As shown in FIGS. 13 and 14, the heat resistant sheath 3 for endoscope in the present case has one observation opening portion 27a provided at the sheath distal end portion 27, and a reduced diameter portion 29, which is the observation opening portion 27a whose diameter around the whole circumference is reduced compared to the main body sheath 25, is provided.

Note that the observation opening portion 27a here is formed at a position that is point symmetrical to the exhaust opening portion 27b with respect to any point on the central axis of the sheath distal end portion 27, that is, at a position rotated around the outer circumference by 180 degrees.

Furthermore, as shown in FIG. 14, the reduced diameter portion 29 of the sheath distal end portion 27 has an inner diameter d4 smaller than the inner diameter d1 of the main body sheath 25, and the distal end side of the sheath distal end portion 27 with respect to the reduced diameter portion 29 has a shape with the same inner diameter d1 as the main body sheath 25.

According to such a configuration, at the time of observation by the endoscope system 1, a phenomenon occurs at the sheath distal end portion 27 of the heat resistant sheath 3 for endoscope, according to which the flow velocity of the compressed air A from the air compressor 24 for cooling the insertion portion 4 is increased at the time of the compressed air A passing through the reduced diameter portion 29 due to the so-called Venturi effect, and the outside air A' near the observation opening portion 27a is slightly drawn into the sheath distal end portion 27. Slight negative pressure is caused by the phenomenon at the observation opening portion 27a in the opposite direction from the observation direction of the endoscope apparatus 2.

Accordingly, the compressed air A fed to the sheath distal end portion 27 is hardly discharged in the observation direction of the endoscope apparatus 2 from the observation opening portion 27a, and is discharged mainly from the exhaust opening portion 27b provided on the distal end side with respect to the observation opening portion 27a.

Fifth Modification

As shown in FIG. 15, the heat resistant sheath 3 for endoscope in the present case has a constricted portion 27c with a reduced diameter, in the circumferential direction, formed in the sheath distal end portion 27 of the main body sheath 25. A plurality of observation opening portions 27a are formed at a distal end of the constricted portion 27c. Moreover, the constricted portion 27c has an inner diameter d5 smaller than the inner diameter d1 of the main body sheath 25.

Also according to such a configuration, at the time of observation by the endoscope system 1, a phenomenon occurs at the heat resistant sheath 3 for endoscope, according to which the flow velocity of the compressed air A from the air compressor 24 for cooling the insertion portion 4 is increased at the time of the compressed air A passing through the constricted portion 27c due to the so-called Venturi effect, and the outside air A' near the observation opening portion 27a is slightly drawn into the sheath distal end portion 27. Slight negative pressure is caused by the phenomenon at the observation opening portion 27a in the opposite direction from the observation direction of the endoscope apparatus 2.

Accordingly, the compressed air A fed to the sheath distal end portion 27 is hardly discharged in the observation direction of the endoscope apparatus 2 from the observation opening portion 27a, and is discharged mainly from the exhaust opening portion 27b provided on the distal end side with respect to the observation opening portion 27a.

Sixth Modification

As shown in FIGS. 16 and 17, the heat resistant sheath 3 for endoscope in the present case is provided, at the distal end of the main body sheath 25, with a bottomed cylindrical sheath distal end portion 51 that is provided with one observation opening portion 51a.

As shown in FIG. 17, the sheath distal end portion 51 has an inner diameter d6 smaller than the inner diameter d1 of the main body sheath 25, and an exhaust opening portion 51b as an exhaust hole is formed in the sheath distal end portion 51, on the distal end side with respect to the observation opening portion 51a.

A male screw portion 51c, of the sheath distal end portion 51, formed on a proximal end outer circumferential portion is threadedly attached to a female screw portion 25b formed in a distal end inner circumferential portion of the main body sheath 25, and the sheath distal end portion 51 is connected to a distal end opening of the main body sheath 25.

Note that, also in the present case, the exhaust opening portion 51b is formed at a position that is point symmetrical to the observation opening portion 51a with respect to any point on the central axis of the sheath distal end portion 51, that is, at a position rotated around the outer circumference by 180 degrees.

Also according to such a configuration, at the time of observation by the endoscope system 1, a phenomenon occurs at the heat resistant sheath 3 for endoscope, according to which the flow velocity of the compressed air A from the air compressor 24 for cooling the insertion portion 4 is increased due to the so-called Venturi effect, and the outside air A' near the observation opening portion 51a is slightly drawn into the sheath distal end portion 51. Slight negative pressure is caused by the phenomenon at the observation opening portion 51a in the opposite direction from the observation direction of the endoscope apparatus 2.

Accordingly, the compressed air A fed to the sheath distal end portion 51 is hardly discharged in the observation direction of the endoscope apparatus 2 from the observation opening portion 51a, and is discharged mainly from the exhaust opening portion 51b provided on the distal end side with respect to the observation opening portion 51a.

Seventh Modification

As shown in FIGS. 18 and 19, the heat resistant sheath 3 for endoscope in the present case includes, at the sheath distal end portion 27 of the main body sheath 25, one observation opening portion 27a, the exhaust opening portion 27b formed at a position point symmetrical to the observation opening portion 27a with respect to any point on the central axis of the sheath distal end portion 27, that is, at a position rotated around the outer circumference by 180 degrees, and a conduit portion 52 provided along a longitudinal direction from the sheath distal end portion 27 to the main body sheath 25.

Note that the conduit portion 52 is a member which is semi-circular in cross section, with a closed distal end and which covers approximately half the outer circumferential portion of the main body sheath 25 including the sheath distal end portion 27 so as to cover the exhaust opening portion 27b. Also, the conduit portion 52 is open on the proximal end side of the main body sheath 25, which is an operator's side.

According to the heat resistant sheath 3 for endoscope having such a configuration, at the time of observation by the endoscope system 1, the compressed air A from the air compressor 24 for cooling the insertion portion 4 flows from the exhaust opening portion 51b provided on the distal end side with respect to the observation opening portion 51a into the conduit portion 52, and is discharged from the opening on the proximal end side of the main body sheath 25. Accordingly, because the compressed air A is not discharged into an examination part being observed by the endoscope apparatus 2, accurate examination may be performed without greatly changing the environment of the examination target.

Eighth Modification

As shown in FIGS. 20 and 21, the heat resistant sheath 3 for endoscope in the present case is provided with a cylindrical body 53 which covers a distal end outer circumferential portion of the sheath distal end portion 27 of the main body sheath 25. The cylindrical body 53 has an inner diameter that is larger than the outer diameter of the sheath distal end portion 27, and is provided in a manner covering only the distal end side of the sheath distal end portion 27 so as not to cover a plurality of observation opening portions 27a.

That is, the cylindrical body 53 is fixed to the sheath distal end portion 27 with an inner circumferential surface separated from an outer circumferential surface of the sheath distal end portion 27 by a predetermined distance. Also, the cylindrical body 53 is sealingly fixed to the sheath distal end portion 27 with a distal end coinciding with a distal end position of the sheath distal end portion, and an opening portion 53a is formed at a position overlapping the exhaust opening portion 27b of the sheath distal end portion 27.

According to the heat resistant sheath 3 for endoscope having such a configuration, at the time of observation by the endoscope system 1, even if the compressed air A from the air compressor 24 for cooling the insertion portion 4 spreads outside the main body sheath 25 of the guide main body 21 at the time of passing through the plurality of observation opening portions 51a, air A" flows in from a proximal end of the cylindrical body 53, and is discharged from the opening portion 53a of the cylindrical body 53 together with the compressed air A discharged from the exhaust opening portion 27b of the sheath distal end portion 27.

Ninth Modification

As shown in FIG. 22, the heat resistant sheath 3 for endoscope in the present case is provided with a flexible portion 55, at a distal end part of the rigid main body sheath 25, so as to allow a bending operation of the insertion portion 4 of the endoscope apparatus 2 inserted inside, and with an adapter-type distal end portion 60 that can be freely detached/attached from/to a pipe sleeve 56 provided at a distal end of the flexible portion 55.

The adapter-type distal end portion 60 is configured by having a plurality, such as four, of observation opening portions 61a formed in the circumferential direction, and by including an observation cylindrical portion 61 that can be freely detached/attached from/to the pipe sleeve 56, and a cap 62 to which an exhaust opening portion 62a is formed and that can be freely detached/attached from/to the observation cylindrical portion 61.

A male screw portion 61b configured to threadedly connect to a female screw portion 56a formed on a distal end inner circumference of the pipe sleeve 56 is formed on a proximal end outer circumference of the observation cylindrical portion 61. Also, a female screw portion 61c configured to threadedly connect to a male screw portion 62b formed on a proximal end outer circumference of the cap 62 is formed on a distal end inner circumference of the observation cylindrical portion 61.

According to such a configuration, the heat resistant sheath 3 for endoscope may allow selection and exchange of the adapter-type distal end portion 60 according to different types of endoscope apparatuses 2. Furthermore, the observation cylindrical portion 61 and the cap 62 may also be selectively exchanged for another as appropriate.

Tenth Modification

As shown in FIG. 23, the heat resistant sheath 3 for endoscope in the present case has a cover body 75 fixed to a distal end opening portion of the rigid main body sheath 25. The cover body 75 is fixed to the distal end opening portion of the main body sheath 25 by a screw, an adhesive or the like. The heat resistant sheath 3 for endoscope is thereby configured such that the compressed air A from the air compressor 24 for cooling the insertion portion 4 fed into the main body sheath 25 is not leaked from the distal end opening portion of the main body sheath 25.

As shown in FIG. 24, an endoscope positioning portion 76 having a cylindrical shape is integrally formed with the cover body 75. The endoscope positioning portion 76 has a proximal end part abutted against a distal end part of the endoscope distal end portion 13 inserted into the main body sheath 25 to determine the insertion position of the insertion portion 4 of the endoscope apparatus 2 inside the main body sheath 25.

A plurality, such as four, of opening portions 76a are formed in the endoscope positioning portion 76, in the circumferential direction. Note that the opening portions 76a here are formed at four positions, at every 90 degrees, around the circumference of the endoscope positioning portion 76, but this is not restrictive, and the opening portions 76a may alternatively be formed at two positions, at every 180 degrees.

As in each of the embodiment and the modifications described above, the main body sheath 25 in the present case also includes the exhaust opening portion 27b on the distal end side, and the observation opening portion 27a that is formed on the operator's side and at a position opposite by 180 degrees.

Furthermore, as shown in FIG. 25, the main body sheath 25 is provided, on inner circumferential portions in front and behind the observation opening portion 27a, with a protruding portion 72 and a narrow diameter portion 71 which is formed to have a non-uniform thickness, as shown in FIG. 26, so that an inner diameter center is made eccentric from an outer diameter center according to the position of the protruding portion 72. Note that a tapered surface 71a is formed behind the narrow diameter portion 71.

The insertion portion 4 of the endoscope apparatus 2 is inserted through the main body sheath 25, and is arranged so as to be on the distal end side with respect to the observation opening portion 27a, and thus the flow velocity of the compressed air A flowing through the exhaust opening portion 27b is increased due to the so-called Venturi effect, compared to the compressed air A flowing on the observation opening portion 27a side, and thus the compressed air A may easily flow on the exhaust opening portion 27b side.

That is, the flow velocity of the compressed air A from the air compressor 24 for cooling the insertion portion 4, fed from the operator's side into the main body sheath 25 is increased near the observation opening portion 27a due to the main body sheath 25 being narrowed by the narrow diameter portion 71 and also by the compressed air A flowing along the tapered surface 71a.

As described above, according to the heat resistant sheath 3 for endoscope, because the compressed air A from the air compressor 24 for cooling the insertion portion 4, fed into the main body sheath 25 is not discharged to an examination part being observed by the endoscope apparatus 2, accurate examination may be performed without greatly changing the environment of the examination target.

Note that the insertion portion 4 of the endoscope apparatus 2 is positioned at a position where an outer circumferential portion of the endoscope distal end portion 13 abuts against the protruding portion 72 and the distal end hits the endoscope positioning portion 76, and the proximal end side is fixed by the proximal end pipe sleeve 22 (not shown). The illumination window 11 and the observation window 12 of the endoscope apparatus 2 are thereby positioned to face the observation opening portion 27a.

According to such a configuration, the heat resistant sheath 3 for endoscope may allow positioning of the endoscope apparatus 2, and may allow the compressed air A to easily flow to the discharge side.

The components of each of the embodiment and the modifications described above may be combined. That is, the invention described in the embodiment above is not limited to the embodiment and the modifications, and in the practical stage, various modifications may be made without departing from the spirit of the invention. Furthermore, the embodiment described above includes inventions of various stages, and various inventions may be extracted by appropriately combining the plurality of components disclosed herein.

For example, even if some components are removed from all the components shown in the embodiment, if the problem to be solved can be solved and the advantageous effects stated can be achieved, a configuration from which the components have been removed can be extracted as an invention.

What is claimed is:

1. A heat resistant sheath for endoscope comprising:
a main body sheath having a substantially tubular shape into which at least a distal end side of an insertion portion of an endoscope apparatus is inserted, and into which a cooling fluid for cooling the insertion portion is supplied by a cooling device;
a sheath distal end portion, having a bottomed cylindrical shape with a closed distal end, at which an endoscope distal end portion of the insertion portion inserted into the main body sheath is arranged, and that is connected to a distal end of the main body sheath;
an observation hole formed at a middle part of a circumferential side portion of the sheath distal end portion, and configured to expose an observation window provided at a side portion of the endoscope distal end portion to allow observation of an object; and
an exhaust hole formed in the circumferential side portion of the sheath distal end portion, on a distal end side with respect to the observation hole, and configured to discharge the cooling fluid in a direction different from an observation direction of the endoscope apparatus;
wherein the exhaust hole is formed in the circumferential side portion of the sheath distal end portion at a position symmetrically opposed to a position of the exhaust hole about a longitudinal central axis of the sheath distal end portion.

2. The heat resistant sheath for endoscope according to claim 1, wherein the exhaust hole has a larger opening area than the observation hole.

3. The heat resistant sheath for endoscope according to claim 1, wherein an inner diameter of the sheath distal end portion is smaller than an inner diameter of the main body sheath.

4. A heat resistant sheath for endoscope comprising:
a main body sheath having a substantially tubular shape into which at least a distal end side of an insertion portion of an endoscope apparatus is inserted, and into which a cooling fluid for cooling the insertion portion is supplied by a cooling device;
a sheath distal end portion, having a bottomed cylindrical shape with a closed distal end, at which an endoscope distal end portion of the insertion portion inserted into the main body sheath is arranged, and that is connected to a distal end of the main body sheath;
an observation hole formed at a middle part of a circumferential side portion of the sheath distal end portion, and configured to expose an observation window provided at a side portion of the endoscope distal end portion to allow observation of an object; and
an exhaust hole formed in the circumferential side portion of the sheath distal end portion, on a distal end side with respect to the observation hole, and configured to discharge the cooling fluid in a direction different from an observation direction of the endoscope apparatus;
wherein the sheath distal end portion is configured by an inner cylinder, having a cylindrical shape, connected to the main body sheath and with an open distal end, and an outer cylinder, having a bottomed cylindrical shape, disposed to cover the inner cylinder and with a closed distal end, and
the observation hole is formed in each of the inner cylinder and the outer cylinder, at overlapping positions.

5. The heat resistant sheath for endoscope according to claim 4, wherein the outer cylinder has an inner diameter larger than an outer diameter of the inner cylinder, and is fixed to the inner cylinder with a clearance.

6. The heat resistant sheath for endoscope according to claim 5, wherein the outer cylinder is fixed eccentrically with respect to the inner cylinder.

7. An endoscope system comprising:
the endoscope apparatus and the cooling device; and
the heat resistant sheath for endoscope according to claim 1.

8. An endoscope system comprising:
the endoscope apparatus and the cooling device; and
the heat resistant sheath for endoscope according to claim 4.

* * * * *